US006984488B1

(12) United States Patent
Gershoni et al.

(10) Patent No.: US 6,984,488 B1
(45) Date of Patent: Jan. 10, 2006

(54) DETERMINATION AND CONTROL OF BIMOLECULAR INTERACTIONS

(75) Inventors: Jonathan M. Gershoni, Rehovot (IL); David Enshel, Givatayim (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 09/297,668

(22) PCT Filed: Nov. 4, 1997

(86) PCT No.: PCT/IL97/00353

§ 371 (c)(1),
(2), (4) Date: May 6, 1999

(87) PCT Pub. No.: WO98/20169

PCT Pub. Date: May 14, 1998

(30) Foreign Application Priority Data

Nov. 7, 1996 (IL) .................................... 119586

(51) Int. Cl.
*C12Q 1/68* (2006.01)
(52) U.S. Cl. ...................... 435/6; 435/69.7; 435/68.1; 435/69.1; 435/70.1; 435/71.1; 530/300; 530/317; 536/23.1; 536/25.3; 536/23.4; 536/23.53
(58) Field of Classification Search .................... 435/6, 435/69.7, 68.1, 69.1, 70.1, 71.1, 320.1; 530/300; 536/317, 23.1, 25.3, 23.4, 23.53; 436/536
See application file for complete search history.

(56) References Cited

U.S. PATENT DOCUMENTS 5,691,170 A * 11/1997 Gritz et al. ................ 435/69.7
5,811,238 A * 9/1998 Stemmer et al. ............... 435/6
6,031,071 A * 2/2000 Mandeville et al. ........ 530/300

FOREIGN PATENT DOCUMENTS

WO WO 98/05764 * 2/1998

OTHER PUBLICATIONS

Huse et al "Generation of a large combinatorial library of the immunoglobulin repertoire in pahge lambda" Science, Dec. 8, 1989, 246: 1275-1281.*
Marks et al "Molecular evolution of proteins on filamentous phage" The Journal of Biological Chemistry, Aug. 15, 1992, 267(23): 16007-16010.*
Wang et al, "Use of a Gene-Targeted Phage Display Random Epitome Library to Map an Antigenic Determinant on the Bluetongue Virus Outer Caspid Protein VP5", *J. Immun. Methods,* 178: 1-12, 1995.
Ulmer et al, "DNA Vaccines", *Curr. Opin. Immun.,* 8: 531-536, 1996.
Ulmer et al, "ELI's Coming: Expression Library Immunization and Vaccine Antigen Discovery", *Trends in Microbiology,* 4(5): 169-170, 1996.
Pasqualini et al, "Organ Targeting *in vivo* Using Phage Display Peptide Libraries", *Nature,* 380 364-366, 1996.
Willis et al, "Immunological Properties of Foreign Peptides in Multiple Display on a Filamentous Bacteriophage", *Gene,* 128: 79-83, 1993.
Cortese et al, "Epitope Discovery Using Peptide Libraries Displayed on Phage", *TIBTECH,* 12:262-266, 1994.
Lane et al, "Epitope Mapping Using Bacteriophage Peptide Libraries", *Curr. Opin. Immun.,* 5: 268-271, 1993.
Baughn et al, "Epitope Mapping of B-Cell Determinants on the 15-Kilodalton Lipoprotein of *Treponema Pallidum* (Tpp15) with Synthetic Peptides", *Infection and Immunity,* 64(7): 2457-2466, 1996.
Dybwad et al, "Identification of New B Cell Epitopes in the Sera of Rheumatoid Arthritis Patients Using a Random Nanopeptide Phage Library", *Eur. J. Immunol.,* 23: 3189-3193, 1993.
Dybwad et al, "Structural Characterization of Peptides that Bind Synovial Fluid Antibodies from RA Patients: A Novel Strategy for Identification of Disease-Related Epitopes Using a Random Peptide Library", *Clin. Immunol. And Immunopathol.;* 75(1): 45-50, 1995.
Folgori et al, A General Strategy to Identify Mimotopes of Pathological Antigens Using Only Random Peptide Libraries and Human Sera, *The EMBO Journal,* 13(9): 2236-2243, 1994.
Felici et al, "Selection of Antobody Ligands from a Large Library of Oligopeptides Expressed on a Multivalent Exposition Vector", *J. Moi. Biol.,* 222: 301-310, 1991.
Mougneau et al, "Expression Cloning of a Protective *Leishmania* Antigen", *Science,* 268: 563-566, 1995.
Ho et al, "Discontinuous Epitopes on gp120 Important in HIV-1 Neutralization", *Aids Research and Human Retroviruses,* 8(8): 1337-1339, 1992.
Thali et al, "Characterization of a Discontinuous Human Immunodeficiency Type 1 gp 120 Epitope Recognized by a Broadly Reactive Neutralizing Human Monoclonal Antibody", *J. Virology,* pp 6188-6193, 1991.

(Continued)

*Primary Examiner*—Jeffrey Fredman
(74) *Attorney, Agent, or Firm*—Browdy and Neimark, PLLC

(57) ABSTRACT

Methods of using overlapping peptides for the discovery of discontinuous epitopes, as vaccines, for drug design, for diagnostic purposes and for the elucidation of three-dimensional protein structure. Specifically, these methods can be used to map conformational epitopes using overlapping peptides. The methods are both complete, yet more specific than random phage libraries. They can also be used to develop DNA vaccines which exploit the concept of overlapping peptides in a variety of expression systems. Conformational epitopes prepared with these methods can be used for preparing antibodies, as components of diagnostic tools, and for elucidating three-dimensional protein structure.

11 Claims, No Drawings

OTHER PUBLICATIONS

Oravecz et al, "β-Chemokine Inhibition of Monocytropic HIV-1 Infection", *J. Immunol.*, 157: 1329-1332, 1996.

Ho et al, "Conformational Epitope on gp 120 Important in CD4 Binding and Human Immunodeficiency Virus Type 1 Neutralization Identified by a Human Monoclonal Antibody", *J. Virology*, pp 489-493, 1991.

Bachelder et al, Postbinding Functions of CD4 in HIV Infection, *Trends in Microbiology*, 4(9): 359-363, 1996.

Ho et al, "Another Discontinuous Epitope on glycoprotein gp120 that is Important in Human Immunodeficiency Virus Type 1 Neutralization is Identified by a Monoclonal Antibody", *Proc. Natl. Acad. Sci. USA*, 88: 8949-8952, 1991.

Thali et al, "Discontinuous, Conserved Neutralization Epitopes Overlapping the CD4-Binding Region of Human Immunodeficiency Virus Type 1gp120 Envelope Glycoprotein", *J. Virology*, pp 5635-5641, 1992.

Stemmer, WPC, "Rapid Evolution of a Protein *in vitro* by DNA Shuffling", *Nature*, p389, 1994.

Matsumura et al, "DNA Shuffling Brightens Prospects for GFP", *Nature Biotechnol.*, 14: 366, 1996.

Crameri et al, "Improved Green Fluorescent Protein by Molecular Evolution Using DNA Shuffling", *Nature Biotechnol.*, 14: 313, 1996.

Cortese et al, "Identification of Biologically Active Peptides Using Random Libraries Displayed on Phage", *Curr. Opinion in Biotechnol.* 6: 73-80, 1995.

Oldenburg et al, "Peptide Ligands for a Sugar-Binding Protein Isolated from a Random Peptide Library", *Proc. Natl. Acad. Sci. USA*, 89: 5393-5397, 1992.

Scott et al, A Family of Concanavalin A-Binding Peptides from a Hexapeptide Epitope Library, *Proc. Natl. Acad. Sci. USA*, 89: 5398-5402, 1992.

Hoess et al, "Identification of a Peptide Which Binds to the Carbohydrate-Specific Monoclonal Antibody", *Gene*, 128: 43-49, 1993.

Greenwood et al, "Multiple Display of Foreign Peptides on a Filamentos Bacteriophage", J. Mol. Biol. 320: 821-827, 1991.

Falt et al, "Epitope Mapping of Six Monoclonal Antibodies Recognizing the *Shigella Dysenteriae* Type O-Antigenic Repeating Unit Expressed in *Escherichia Coli* K-12", *Microbial. Pathenogenesis*, 16: 27-41, 1994.

Sioud et al, Characterization of Naturally Occurring Autoantibodies Against Tumoour Necrosis Factor-Alpha (TNF-α: *in vitro* Function and Precise Epitope Mapping by Phage Epitope Library, *Clin. Exp. Immunol.*, 98: 520-525, 1994.

Gao et al, "Multiple Interactive Residues of Recognition",*J. Immunol.*, 157: 183-188, 1996.

Launois et al, "T-Cell Epitope Mapping of the Major Secreted Mycobacterial Antigen Ag85A in Tuberculosis and Leprosy", *Infection and Immunity*, pp. 2679-3687, 1994.

Putkonen et al, "Prevention of HIV-2 and $SIV_{sm}$ Infection by Passive Immunization in Cynomolgus Monkeys", Nature, 253: 436-437, 1991.

de la Cruz et al, "Immunogenicity and Epitope Mapping of Foreign Sequences via Genetically Engineered Filamentous Phage", *J. Biological Chem.* 263(9): 4318-4322, 1988.

Luzzaga et al, "Mimicking of Discontinuous Epitopes by Phage-Displayed Peptides, I. Epitope Mapping of Human H Ferritin Using a Phage Library of Constrained Peptides", Gene, 1993, pp 51-57.

Maliszewski et al, "The CD39 Lymphoid Cell Activation Antigen", *J. Immunol.*, 153:3574-3583, 1994.

Graf et al, "Random circular permutation of genes and expressed polypeptide chains: application of the method to the catalytic chains of aspartate transcarbamoylase", *Proc Natl Acad Sci USA* 93(21):11591-11596 (1996).

Nagesha et al, "Application of linker-ligation-PCR for construction of phage display epitope libraries", *J Virol Methods* 60(2):147-154 (1996).

Crameri et al, "Display of expression products of cDNA libraries on phage surfaces. A versatile screening system for selective isolation of genes by specific gene-product/ligand interaction", *Eur J Biochem* 226(1):53-68 (1994).

Du Plessis et al, "Identification of an antigenic peptide specific for bluetongue virus using phage display expression of NS1 sequences," *Immunotechnology* 1(3-4):221-230 (1995).

Jacobsson et al, "Cloning of ligand-binding domains of bacterial receptors by phage display", *Biotechniques* 18(5): 878-885 (1995).

Jacobsson et al, "Phage display shot-gun cloning of ligand-binding domains of prokaryotic receptors approaches 100% correct clones", *Biotechniques* 20(6): 1070-1076, 1078, 1080-1081 (1996).

* cited by examiner

DETERMINATION AND CONTROL OF BIMOLECULAR INTERACTIONS

FIELD AND BACKGROUND OF THE INVENTION

The present invention relates to the determination and control of bimolecular interactions and, more particularly, to the exploitation of these interactions for the production of new pharmaceuticals, such as vaccines, and diagnostic or research assays, such as antibody-based assays.

Bimolecular interactions are important for a variety of biological processes, including pathological processes. Such interactions typically involve the recognition of a three-dimensional structure, such as a protein, carbohydrate or drug ligand, by another such structure. Nature performs with ease many such interactions, which so far have proven largely refractory to analysis. Such difficulty has had a negative impact on the fields of vaccine and drug development in particular, which have had to rely on a trial-and-error approach, in the absence of defined rules for the production of novel vaccines and other pharmaceuticals. However, such trial-and-error approaches are costly and inefficient. Clearly, new approaches are needed in these fields.

The problem of vaccine and drug development, which is associated with bimolecular interactions, can be narrowed to the interaction between specific epitopes on the two molecules involved. In the case of two proteins, these epitopes can be composed of particular peptides, or of peptides and carbohydrates. For a drug and its receptor, these epitopes may consist of peptides on the receptor, and functional groups on the drug. These different materials would appear to indicate that these different types of bimolecular interactions would require different systems for study. However, as described below, all of these different epitopes can be mimicked by peptides. Thus, a single system for screening large numbers of peptides could be employed to explore all of these different types of epitope interactions, since all of these interactions could be represented by different types of peptide libraries. For example, peptides which mimic a carbohydrate could be found using a random peptide library, which contains all possible peptides of a given length. Alternatively, an antigen library could be used to represent peptides derived from the primary sequence of an antigen, such as a protein, for example. If such an antigen library represented all possible peptides of a given-length contained within the protein, the library could be said to represent a complete pepscan of the antigen.

Such a complete pepscan could be found in a reference by Baughn et al. [Baughn, R. E., Demecs, M., Taber, L. H. and D. M. Musher, Infection and Immunity, 1996, 64:2457–2466] for the 15-kDa lipoprotein of *Treponema pallidum*, which causes syphilis. Overlapping decapeptides (ten amino acids) were synthesized, each of which overlapped the next by nine amino acids, and were offset by one amino acid, so that a complete set of decapeptides was obtained. These were then screened with sera from syphilitic rabbits in an ELISA (enzyme-linked immunosorbent assay), to find those peptides which reacted with antibodies against syphilis. The limitations to such an approach are immediately obvious, particularly since the synthesis of such a large number of peptides is both tedious and difficult to manage. Clearly, producing complete pepscans by peptide synthesis limits the approach for small proteins. Indeed, Baughn et al. note that their choice of protein was strongly influenced by size.

Thus, a new approach to the exploration of bimolecular interactions, and by extension to the fields of vaccine and drug development, is required. This approach uses combinatorial phage display peptide libraries to quickly sort through a huge number of peptides to find those peptides of interest, by a screening assay which functionally selects for a particular behavior in a peptide, as described by G. P. Smith and J. K. Scott [Scott, J. K. and G. P. Smith, Science, 1990, 249:386–390 and Smith, G. P. and J. K. Scott, Methods in Enzymol., 1993, 217:228–257]. For example, to find peptides which bind a particular protein, a phage display peptide library can be affinity-purified using that protein, and then reinfected into bacteria to make more phage containing those peptides of interest. Thus, two problems are solved simultaneously. First, a huge number of peptides can be screened in a single assay. Second, those peptides of interest can be enriched simply by infecting bacteria with the phage containing those peptides, and using the biological machinery of the bacteria to make more phages of interest. Thus, combinatorial phage display peptide libraries can do quickly and easily what artificial laboratory techniques cannot.

Such phage display peptide libraries are typically constructed in the following manner. Phages consist of DNA surrounded by coat proteins, which enable the phage to infect host bacteria and replicate themselves, producing many copies of the phage. To exploit this property, DNA sequences coding for the peptide of interest are inserted into the gene coding for a phage coat protein. As long as these insertions do not interfere with the life cycle of the phage, these modified phages will have coat proteins which display the foreign peptide. Filamentous phages are the preferred vectors, because two of their coat proteins can be easily modified to display foreign peptides, and thus foreign epitopes, on their surface. In general, these modifications are well tolerated. However, even if the modifications are not tolerated, the phage can still be rescued by a variety of techniques, including co-infection with a wild-type phage, known in the art as a helper phage.

The two coat proteins of the filamentous phage of types such as M13, fd and f2 are known as pIII and pVIII. There are only five copies of pIII on the phage coat, while there are about 2700 copies of pVIII on the coat. However, pIII can generally tolerate large insertions of up to a few hundred amino acids in length, while pVIII can tolerate only five or six amino acid insertions. As noted above, other techniques can be used to rescue phage with pVIII proteins containing larger insertions.

There are two divergent methods for selecting the group of peptides which are to be inserted into the phages to form the phage library. The first type of peptide group is selected according to a known DNA or protein sequence, and forms a series of overlapping peptides. These protein-derived peptides can be used to represent a protein epitope or an entire protein. The second type of peptide group is a partial or complete set of random oligonucleotides. The first group is clearly most useful for a defined problem; for example, the mapping of a particular epitope. The second group is clearly useful when an amino acid sequence for an epitope is unknown, discontinuous in the primary amino acid sequence, or as in the case for complex carbohydrate epitopes, non-existent. In the last case, peptides, called mimotopes, have been found which mimic a selected carbohydrate epitope.

The use of each of these groups of peptides can be most easily demonstrated with reference to the field of vaccine development. Vaccinology is based upon the discovery of epitopes within the pathogen of interest which can be used to elicit an immune response which can neutralize that pathogen. Once these epitopes have been found, they can be presented to the immune system as an active vaccine, to prime the immune system against future infection, in most cases, without causing any infection or pathology themselves. Alternatively, antibodies which bind these epitopes can be isolated and administered as a passive vaccine. Thus, vaccinology depends upon the screening of large numbers of epitopes, in the hope of finding such "neutralizing epitopes", and as such is clearly amenable to the phage display library approach.

One example is the screening of random peptide phage libraries with purified antibodies or sera from humans or animals which have been challenged with a particular pathogen or with an antigen of that pathogen. For example, sera from human patients immunized against a hepatitis B viral antigen, an envelope protein from the virus, were used to screen a random library of nonapeptides (peptides of nine amino acids) inserted into the coat protein pVIII. Phages were selected which contained a nonapeptide that was both an antigenic and an immunogenic mimic of the actual viral antigen [Folgori, A. et al., EMBO, 1994, 13:2236–2243]. Such an approach has also been used in diseases where specific antigens are not known, in an effort to map those antigenic epitopes which react with antibodies in sera which have been raised against the pathogen itself.

The use of protein or antigen derived phage libraries represents a more pathogen-specific approach. The advantage of the antigen derived approach is that the peptides presented by the phage are all related to the pathogen of interest, unlike the random peptide approach, in which many of the peptides will not represent any portion of the pathogen. Thus, a higher proportion of the phages will contain peptides with potentially useful information.

An example of the use of antigen derived phage libraries to map an antigen is given by Wang et al. [Wang et al., J. Immun. Methods, 1995, 178:1–12] for the bluetongue virus outer capsid protein VP5. Bluetongue virus infects sheep and cattle. VP5 is a known antigen for this virus and is 526 amino acids in length. The VP5 gene was partially digested using DNAase I, an enzyme which cuts DNA relatively randomly. The resulting DNA fragments were sorted by size, and those of about 100–200 bp were inserted into the phage pIII gene, and expressed in a phage display library. This library was screened with a monoclonal antibody to find those peptides of the VP5 protein which bind to that antibody and two different peptides were found. As estimated by the authors, this library contained about 200 different peptides, including those peptides representing the vector itself. Thus, only about 70 peptides represented the actual antigen. However, in order for every possible peptide of 30–70 amino acids contained within the VP5 protein to be represented, at least 450 different peptides would be required. Thus, this library did not even completely represent a single known antigen with overlapping peptides. A much more extensive library would be needed to represent all overlapping peptides of a given length within the antigen, thus generating a complete pepscan.

Phage libraries do not need to be used simply for mapping epitopes, however. Perham and colleagues [Greenwood, J., Willis, A. E. and R. N. Perham, J. Mol. Biol., 1991, 220:821–827; and Willis, A. E., Perham, R. N. and D. Wraith, Gene, 1993, 128:79–83] have suggested that peptide epitopes displayed by phage can act as antigens. Discrete peptides obtained from the major surface protein of the malaria parasite *Plasmodium falciparum* were injected into mice, and were successfully immunogenic, causing specific antibodies to be raised against these discrete peptides. However, the peptides used were few in number, and no suggestion was made that an entire phage library could be used as a vaccine.

An alternative to the use of phages to display peptides which correspond to inserted DNA fragments is to use the DNA fragments themselves in a DNA vaccine. DNA vaccines are, as their name suggests, composed of DNA which can stimulate antigen-specific immunity within an animal. The DNA in question must code for the antigen of interest. Such DNA vaccines include the expression library immunization system (ELI) or naked DNA vaccines. As noted in Ulmer et al. [Ulmer et al., Curr. Op. Immunol., 1996, 8:531–536], naked DNA vaccines have been shown to be effective against influenza virus in animals. A particular bonus of these naked DNA vaccines is that they can elicit cellular as well as antibody responses, which many conventional vaccines cannot.

The expression library immunization system (ELI) also uses naked DNA coding for those proteins expressed by a particular pathogen, as described by Barry et al. [Barry et al., Nature, 1995, 377:632–635]. Alternatively, proteins expressed in bacteria have been used to present recombinant proteins to the immune system, as described by Mougneau et al. [Mougneau et al., Science, 1995, 268:563–566]. However, both of these methods are somewhat limited in power as compared to complete pepscans, since complete pepscans can cover substantially every possible continuous epitope of a pathogen, while these other methods only present specific proteins from a pathogen. Furthermore, as noted by Barry et al., large amounts of naked DNA were required for immunization.

Phage can also be used to present peptides for non-vaccine related interactions. Random peptide phage libraries have been used to target organs in vivo by Pasqualini and Ruoslahti [Pasqualini, R. and E. Ruoslahti, Nature, 1996, 380:364–366]. In their experiments, an entire random peptide phage library was injected into mice, and the mice were sacrificed 1–4 minutes later. Thus, although phage carrying specific peptides successfully targeted particular organs, the time frame did not permit any immunogenic effect to be observed, nor was such a potential effect even mentioned or intended by the authors.

Random peptide phage libraries have an additional advantage over more specific complete pepscans of an antigen. Random phage libraries can be used to map discontinuous epitopes, while a complete pepscan can be used to map continuous epitopes of an antigen, because of the nature of the group of peptides represented. A continuous epitope can be defined as one in which the antigenic residues reside within a short sequence of amino acids, less than from about ten to about fifteen amino acids. This sequence should definitely not be any longer than the length of the average peptide. Thus, only those epitopes which are continuous will be mapped. However, many epitopes have been shown to be discontinuous. These epitopes are composed of peptides derived from different positions in the primary sequence, but which are adjacent in the three-dimensional structure of the protein. An antigen-derived peptide display library of relatively short peptides does not contain peptides which represent these epitopes.

An example of the importance of discontinuous epitopes is in the study of HIV, or human immunodeficiency virus. HIV causes almost invariably fatal disease in humans; so far, no cure or vaccine has been found. An important step in HIV infection is the binding of an HIV envelope protein, gp120, to the T-cell receptor CD4. CD4 may also be important in post-binding events in HIV infection. Indeed, it has been suggested that CD4 changes conformation in response to HIV binding, and that this altered conformation may also be responsible for post-binding infection events. Thus, the interaction of gp120 with CD4 is a natural target for vaccine design.

Part of the difficulty in finding such a vaccine, however, is that the major neutralizing epitope, the V3 region of gp120, is hypervariable, so that antibodies raised against this region tend to be specific for one type of HIV and not others. Antibodies have been found with much broader specificity, several of which clearly bind to discontinuous gp120 epitopes. Thus, such discontinuous epitopes are obvious targets for mapping, as an aid to vaccine design.

As noted above, random peptide phage libraries have been used to map discontinuous epitopes in a variety of systems. Cortese et al. [Cortese et al., Tibtech, 1994, 6:73–80] review a number of discontinuous epitopes which have been found using random peptide phage libraries. However, screening such libraries with sera has not always produced significant results, probably because of the low or incomplete representation of all discontinuous epitopes. In order to overcome this problem, a refinement of the random peptide phage library approach uses constrained peptides, in which amino acids inserted around the random peptide define a particular structure for the peptide to assume, for example a loop structure. However, this approach forces specific structures to be selected, if all random peptides are to be screened. Alternatively, the sequence of the peptide can be held constant, and those surrounding amino acids which determine the structure of the peptide can be varied. In either case, a great deal of the power of random peptide phage libraries, namely the ability to search a broad group of epitopes, is reduced. Thus, more refined discontinuous epitope mapping approaches are clearly needed, which combine the power of random peptide phage libraries with the specificity of antigen-derived phage libraries.

Carbohydrate-protein interactions have also been studied using random peptide phage libraries because of the ability of such libraries to potentially represent discontinuous epitopes of the carbohydrates themselves. These interactions are important for a number of biological processes, including lymphocyte migration and binding of the hemagglutinin protein of the human influenza virus to erythrocyte glycoproteins, an important step in infection by the virus. However, these interactions have typically been difficult to study, because of the difficulty in synthesizing complex carbohydrate ligands. To solve this problem, peptides can be found which mimic carbohydrate ligands. These peptides are also called "mimotopes" because of their mimicry of the carbohydrate epitopes. For example, Oldenburg et al. [Oldenburg et al., PNAS, 1992, 89:5393–5397] used a random octapeptide (eight amino acid) phage library and screened these phage for the ability of the peptide to bind the carbohydrate-binding protein concanavalin A. A group of peptides were found which bound to the protein, although many of these peptides had no obvious sequence homology.

The interactions of many different molecules with proteins, including carbohydrates and drugs, could be much more easily elucidated if the three-dimensional structure, or tertiary native conformation, of the protein were known. Currently, these structures have generally been determined by using X-ray crystallography. However, as its name suggests, this method requires the protein to be capable of forming usable crystals, which are non-trivial to prepare. Indeed, many proteins do not form satisfactory crystals at all, including the vast majority of membrane-spanning proteins, such as neurotransmitter receptors. To overcome this barrier, a number of attempts have been made to use algorithms to predict the three-dimensional structure of a protein from its primary amino acid sequence, as described in *Protein Folding*, ed. by N. Jaenicke, p. 167–181, Amsterdam, Holland (1980), or Computer-Assisted Modeling of Receptor-Ligand Interactions, Theoretical Aspects and Applications to Drug Design, ed. by R. Rein and A. Golombek, 1989, Alan R. Liss, New York for example. Commercially available algorithms include those from MSI, United Kingdom, including Quanta, Delphi and Charmm. However, these algorithms have generally failed to adequately predict the three-dimensional structure of the protein, simply because there are many theoretical structures or conformers to examine, and the rules of protein folding are not completely known.

A compromise between these two approaches has been the use of laboratory experiments to obtain information about the protein itself, which can then be used to place constraints on such protein structure determinations. Such information can be obtained by NMR (Nuclear Magnetic Resonance), which provides information about the interactions of atoms within the protein in the form of distance constraints, although the distances between atoms must be relatively short (less than about 5 Å). However, NMR suffers from lack of specificity; that is, the interactions of too many atoms are all presented simultaneously, making it difficult to decipher the behavior of individual atoms. Furthermore, NMR requires vast amounts of highly purified protein and is also only suitable for water soluble protein.

Alternatively, electron diffraction techniques can be used for a small number of proteins, specifically those membrane-spanning proteins which are highly concentrated within the membrane, such as bacteriorhodopsin.

One method which might be more generally applicable was described in a study by E. Haas [E. Haas, Computer-Assisted Modeling of Receptor-Ligand Interactions, Theoretical Aspects and Applications to Drug Design, ed. by R. Rein and A. Golombek, 1989, Alan R. Liss, New York, p. 157–170]. This method uses the interaction of fluorescent dye molecules attached to particular residues within the protein to obtain information about the structure of the protein. However, this method requires that the protein be purified and labelled with dye molecules, which are both non-trivial procedures.

Once these constraints have been obtained, algorithms are available which use this information to predict the three-dimensional structure of a protein, or at the very least to eliminate those theoretical structures which are not compatible with the experimental evidence. Obviously, as the number of constraints is increased, the predictive ability of these algorithms will be improved correspondingly. Furthermore, it has been noted that longer range distance constraints, or constraints between pairs of residues which are relatively further apart along the primary amino acid sequence, are more useful than short range distance constraints, such as those calculated by NMR [Wako, H. and H. A. Scheraga, Macromolecules, 1981, 14:961–969].

Clearly, such algorithms could be improved by finding constraints which both more accurately reflect partial structures of the protein, and which are more easily measured in a laboratory.

There is thus a widely recognized need for, and it would be highly advantageous to have, a system for the discovery of discontinuous epitopes, to be used as vaccines, for drug design, for diagnostic purposes and for the elucidation of three-dimensional protein structure. Specifically, it would be advantageous to have a system to map discontinuous epitopes which is both complete, yet more specific than random phage libraries. It would also be advantageous to develop DNA vaccines which exploit the concept of overlapping peptides and/or discontinuous epitopes in a variety of expression systems. Finally, it would be advantageous to use discontinuous epitopes for preparing antibodies, as components of diagnostic tools, for preparing passive vaccines and for elucidating three-dimensional protein structure.

SUMMARY OF THE INVENTION

According to the present invention there is provided a phage display library, including: (a) a plurality of fragments of a substantially complete digest of substantially the entire genome of an organism; and (b) a plurality of phages, each of the phages containing one of the fragments.

In the following methods, most of the examples will use DNA, rather than RNA, as the genetic material. It will be appreciated, however, that many of these methods could also be used for RNA, so that the use of the term "DNA" is not intended to be limiting in these examples. The term "genome" is hereinafter defined as the complete genetic material of an organism, whether that genetic material is DNA or RNA based.

Preferably, the organism is a pathogen selected from the group consisting of a virus, a bacterium, a yeast and a parasite.

According to further features in preferred embodiments of the invention described below, there is provided a method of preparing a vaccine, including the steps of: (a) preparing a complete pepscan of at least one polypeptide of an organism; and (b) providing a vaccine carrier for the complete pepscan. The vaccine carrier can optionally include a pharmaceutically appropriate buffer. Also optionally, the complete pepscan is produced by synthesizing peptides. Alternatively, the complete pepscan is produced by a plurality of bacteria, the peptides are synthesized by the bacteria. Optionally, the vaccine carrier includes a plurality of phages, the peptides are presented by the phages. Preferably, the phages are filamentous phages and each of the peptides is presented by a coat protein of the filamentous phages. Most preferably, the coat protein is pVIII or pIII. Also alternatively, the vaccine carrier includes an eukaryotic expression vector and the complete pepscan is presented by the vector to be preferably used as a DNA vaccine in which the peptides are ultimately synthesized by the organism to be vaccinated.

According to still further features in preferred embodiments of the invention described below, there is provided a method of vaccinating an organism, including the steps of: (a) preparing a vaccine by the above method; and (b) administering the vaccine to the organism.

According to another embodiment, there is provided a method of preparing a discontinuous library of an organism having a genome, including the steps of: (a) at least partially digesting at least a portion of the genome of the organism to form a plurality of fragments, the portion being characterized as representing at least a part of a single biological unit; and (b) ligating the fragments to form at least one ligated fragment; and (c) at least partially digesting the ligated fragment to form at least one conformational fragment. Preferably, the biological unit is a polypeptide. Also preferably, the method further includes (d) providing a display carrier for the at least one conformational fragment. More preferably, the display carrier includes at least one bacteria and the at least one conformational fragment is inserted into genetic material within the at least one bacteria. Alternatively, the display carrier includes at least one phage and the at least one conformational fragment is inserted into genetic material within the phage. Preferably, the phage is a filamentous phage, and the at least one conformational fragment is inserted into a gene for a coat protein of the filamentous phage. Most preferably, the coat protein is selected from the group consisting of pIII and pVIII. Alternatively, the display carrier includes an eukaryotic expression vector and the at least one conformational fragment is inserted into the vector. Also provided is a discontinuous library of the genome of an organism, including at least one conformational fragment, prepared according to the above method.

According to still further features in the described preferred embodiments, there is provided a method of preparing a conformational peptide, including the steps of: (a) preparing a discontinuous library of an organism according to the above method; (b) inserting the discontinuous library into an expression system; and (c) obtaining the conformational peptide from the expression system. Preferably, the expression system includes at least one bacteria, the discontinuous library is inserted into genetic material of the at least one bacteria. Most preferably, the conformational peptide is obtained from the expression system by isolating the conformational peptide, such that the conformational peptide is at least a partially purified conformational peptide. Alternatively, the expression system includes at least one phage and the discontinuous library is inserted into genetic material of the at least one phage. Also provided is a conformational peptide, including a peptide, the sequence of the peptide being determined by a digestion product of a ligation product of at least two fragments of at least a partial digest of at least a portion of the genome of an organism, the portion representing at least a part of a single biological unit. Optionally, the peptide is obtained from an expression system, the expression system including the digestion product.

According to yet another embodiment, there is provided a method of preparing a vaccine, including: (a) preparing a discontinuous library according to the above method; and (b) providing a vaccine carrier for the discontinuous library. Optionally, the vaccine can then be administered to an organism to be vaccinated.

According to yet another embodiment, there is provided a method of detecting an antibody for binding at least one discontinuous epitope of a single biological unit of a first organism, including the steps of: (a) preparing a screening library of the first organism; and (b) detecting the antibody for binding the discontinuous epitope by screening the screening library with immune material from a second organism. Optionally, the screening library includes a discontinuous library prepared according to the above method, and the immune material is prepared by administering at least a portion of the single biological unit of the first organism to the second organism. Alternatively, the screening library includes at least a portion of the single biological unit of the first organism and the immune material is prepared by administering a discontinuous library prepared according to the above method to the second organism. This antibody can form part of a passive vaccine, in another embodiment, and the vaccine can be administered to an organism to be vaccinated.

According to yet another embodiment, there is provided a diagnostic tool for detecting an organism, including: (a) an antibody for binding at least one discontinuous epitope of the organism, the antibody being prepared by screening a discontinuous library with immune material to detect the antibody, the discontinuous library including at least one digestion product of at least one ligation product of digestion fragments of at least a portion of the genome of the organism, the portion representing at least a part of a single biological unit; and (b) a detection assay for determining when the antibody is bound to the at least one discontinuous epitope of the organism. Preferably, the detection assay employs a detection moiety attached to the antibody. Alternatively, the detection assay employs a gradient, and a location of the antibody within the gradient is dictated by the antibody binding to the at least one discontinuous epitope of the organism. Also alternatively, the detection assay employs a chromatograph, and a location of the antibody within the chromatograph is dictated by the antibody binding to the at least one discontinuous epitope of the organism.

According to still further embodiments, there is provided a method for determining a structure of a protein having an identified gene, including the steps of: (a) preparing a conformational peptide of the protein from the gene according to the above method; (b) screening the conformational peptide with a molecule, the molecule being characterized by having an interaction with the protein; (c) determining a sequence of the conformational peptide; and (d) deducing the structure of the protein from the sequence. Preferably, the molecule is an antibody, the antibody is for binding to at least one discontinuous epitope of the protein. Alternatively, the molecule is a ligand, the ligand is for binding to the protein. Also alternatively, the molecule is a mimotope, the mimotope is for binding a mimotope binding site of the protein.

According to other embodiments of the present invention, there is provided a filter for determining if a theoretical structure of a protein is non-biological, including: (a) a dipeptide juxtaposition of the protein, the dipeptide juxtaposition being determined by a sequence of a conformational peptide of the protein, the sequence being determined by a digestion product of a ligation product of at least two fragments of at least a partial digest of at least a portion of the genome of an organism, the portion being characterized as representing at least a part of a single biological unit; and (b) an algorithm for comparing the dipeptide juxtaposition to the theoretical structure and for determining if the theoretical structure is non-biological.

Finally, in yet another embodiment, there is provided a method of obtaining an antibody for binding at least one discontinuous epitope of a single biological unit of a first organism, including the steps of: (a) preparing a vaccination library of the first organism; (b) administering the vaccination library to a second organism for producing the antibody; and (c) detecting the antibody for binding at least one discontinuous epitope of the single biological unit of the first organism, according to the above method. Preferably, the vaccination library includes at a least a portion of the single biological unit of the first organism and the screening library is a discontinuous library prepared according to the above method. Optionally, the screening library includes at least a portion of the single biological unit of the first organism and the vaccination library is a discontinuous library prepared according to the above method.

DESCRIPTION OF THE PREFERRED EMBODIMENTS

The present invention is of both methods and compositions which can be used to analyze and control bimolecular interactions. Specifically, the present invention includes libraries for both continuous and discontinuous pepscans, which are the basis for a number of products and methods, including both passive and active vaccines and tools for diagnosis and structural analysis.

The invention is illustrated by the following examples, which describe the construction of both continuous and discontinuous pepscan libraries, as well as methods and compositions which use these libraries.

Please note that many experimental protocols, which are well known in the art, are used in the following descriptions but are not described in detail. These prior art protocols are described in a number of protocol and text books. One example of such a book is *Molecular Cloning* by J. Sambrook et al., Cold Spring Harbor Laboratory Press, 1989, which is incorporated by reference as if fully set forth herein for the sole purpose of providing complete descriptions of well known prior art experimental protocols. A further example is Cell Biology ed. by J. E. Celis, Academic Press Inc., 1994.

Example 1

Methods of Constructing a Continuous Complete Pepscan Library

As described in the Background section above, a pepscan includes peptide fragments of a protein or protein(s) of interest. In a complete pepscan, these peptides overlap such that each peptide is offset from the next by one amino acid residue. A pepscan does not need to be limited to a single protein or even a group of proteins. Instead, a pepscan can also be constructed from the entire genome of an organism. Such a pepscan can be described as a continuous pepscan, because it is prepared from peptide fragments which represent continuous epitopes of the primary amino acid sequence of the protein or proteins. A number of methods can be employed to construct such a continuous complete pepscan.

One method involves synthesizing peptides, such that each peptide is offset from the next by one residue. These peptides can be synthesized in a variety of ways including, but not limited to, artificial production by a peptide synthesizing machine.

Another method uses the genome of the organism of interest. First, a substantially complete digest of the genome of the organism of interest is prepared, by digesting the genome so that it is cut into fragments as described hereinbelow. Alternatively, a digest of a portion of the genome of the organism of interest can be prepared, such as a portion of the genome coding for a polypeptide, for example. For example, a complete pepscan of a peptide toxin, such as ricin, venoms including, but not limited to, bungarotoxin or bacterial toxins, might be desirable. Thus, although the following description will refer to "the genome of the organism", it should be understood that a portion of the genome of the organism could also be used. To prepare the digest, typically, DNA is digested by an enzyme which cleaves the DNA strand. For a substantially complete digest of the genome, the enzyme DNAase I is often used. DNAase I cuts DNA relatively randomly; that is, it cuts between any two bases with relatively equal efficiency. When DNAase I is incubated with DNA under appropriate conditions, a collection of fragments of different sizes is obtained which initiate at substantially every single possible base pair. Thus, the genome is represented by DNA fragments which are offset by one base pair. Appropriate conditions are chosen so that a significant fraction of the fragments fall within a desired size range. This collection of fragments is a substantially complete digest of the genome of the organism.

Optionally, such a digest could be prepared by mechanical shearing of the DNA. Such mechanical shearing is well known in the art, and can be accomplished by sonication of the DNA, for example. Mechanical shearing has the further advantage of producing fragments of a more homogeneous size, since shearing forces are greatest in the middle of molecules rather than the edges, and larger molecules are more susceptible to shearing than smaller molecules. However, the cleavage sites are still relatively random, since the genome of the organism is broken relatively randomly during extraction from the organism. One disadvantage of sonication is that the temperature can become very high where the ultrasound waves enter the solution, potentially damaging the DNA.

After the digest has been prepared, the fragments are processed so that all fragment ends are blunt ends, if a blunt-ended vector is used (see below). Those fragments which fall within the desired size range are then separated from the collection of fragments. For example, fragments of from about 50 bp to about 150 bp can be separated by size fractionation. Since only a portion of the collection of fragments from the digest fall within the desired size range, the rest of the fragments are not usable, so a much larger quantity of starting genome material is required to obtain a sufficient quantity of fragments of the desired size range.

Next, a plurality of phages is prepared to receive the group of fragments of the desired size range. This is accomplished by modifying a gene of the phage, so that each fragment can be cloned into the phage gene. The product of that gene, a phage protein, will then include a foreign peptide. The sequence of the foreign peptide will depend upon the inserted DNA fragment. Preferably, a gene for a coat protein is used, so that the phage will display the foreign peptide on its outer surface. Typically, filamentous phages are used because they have coat proteins which are easily modified to receive the foreign DNA fragment. The preferred coat proteins are pIII and pVIII. pIII can tolerate insertions of foreign peptides of up to a few hundred amino acids in length, but only five copies of pIII are on the phage coat. About 2700 copies of pVIII are on the phage coat, but pVIII can only tolerate insertions of up to five or six amino acids, unless special rescue methods are used. The choice of a particular coat protein depends upon both the length of the foreign peptide and upon the desired number of copies per phage of the foreign peptide.

Once the particular coat protein has been chosen, the gene is modified to contain a unique blunt end restriction site, preferably at its N terminal region, using methods which are well known in the art. The particular nature of the restriction site depends upon the strain of phage which is used. For example, for the pIII construct of the fUSE5 vector of the filamentous phage fd-tet such a site could be inserted between the two Sfi-1 sites present on the vector [Scott, J. K. and G. P. Smith, Science, 1990, 249:386–390 and Smith, G. P. and J. K. Scott, Methods in Enzymol., 1993, 217:228–257]. However, it is possible to construct many such blunt-ended phage vectors, by manipulating restriction sites so that DNA fragments can be inserted where desired. Alternatively, oligonucleotide linkers can be used to clone the DNA fragments in distinct and unique restriction sites in the vector which are not necessarily blunt-ended.

Finally, the selected fragments from the digest of the genome of the organism of interest are cloned into the appropriately cut phage vector, using methods which are well known in the art. These phages constitute the phage display library.

A number of factors must be considered in order to ensure that the phage display library contains a complete pepscan of the genome of the organism. Such factors relate to the desired size range of the DNA fragment and the size of the genome of the organism.

The probability of DNAase I randomly digesting the genome so that either end of a resulting DNA fragment is in reading frame is 33.3%. Each DNA fragment can ligate in either one or the other orientation with equal probability. Phages containing a DNA fragment which ends out of reading frame are not viable as the read-through downstream to the inserted fragment will likely terminate prematurely and will definitely generate an irrelevant peptide, instead of the engineered pIII or pVIII proteins. Phages containing a DNA fragment which starts out of reading frame will also probably terminate prematurely due to the appearance of a stop codon.

These factors, when considered collectively, determine that only about one of eighteen, or about five percent of all of the DNA fragments can functionally express relevant peptides. Furthermore, since the DNA fragments must be in reading frame in order to produce a functional peptide, these fragments effectively code for peptides which overlap by about one residue.

One advantage of deriving pepscans from genetic material is that the sequence of the genetic material does not need to be known. As long as DNA is available, it can be digested and expressed in a phage display library, which can include up to from about $10^6$ to about $10^{10}$ phages. The size limitations of such a library easily accommodate even rather large genomes, including those of viruses, bacteria, yeast and parasites. For example, viruses have genomes of from about $10^3$ to about $10^4$ bp or more. Bacteria have genomes of about $10^6$ bp, yeast about $10^7$ bp and parasites from about $10^7$ bp to about $10^8$ bp or more. The size of the library required to accommodate a complete pepscan of the genome of an organism can be calculated according to the following formulas.

$$\text{number of peptides} = \frac{\text{genome size}}{3}$$

$$\begin{array}{c}\text{chances of an inserted fragment}\\ \text{yielding a viable phage}\end{array} = \frac{1}{3} * \frac{1}{3} * \frac{1}{2}$$

$$\text{number of phages} = \frac{\text{genome size} * 18}{3} = 6 * \text{genome size}$$

Of the number of phages initially required for insertion of DNA fragments, only $\frac{1}{18}$ will be viable for an approximately single-fold coverage of the complete pepscan. Greater coverage, such as from about five- to about ten-fold coverage, is preferable. In any case, a complete pepscan of even the entire genome of a parasite of about $10^8$ bp can clearly be accommodated by a single phage display library, since using the above formulas, only about $6*10^8$ phages would be required.

As an example, consider the production of a complete pepscan of the entire HIV (Human Immunodeficiency Virus) genome, which is about 9000 bp. About 3000 peptides of a desired size range would be required in order to have a peptide starting at substantially every possible residue. However, since only about five percent of the inserted DNA fragments can express a functionally relevant peptide, in order to fully represent 3000 peptides for about one-fold coverage, a library of about 60,000 phages is required, of which only about 3000 phages will be viable. Libraries of up to from about $10^9$ to about $10^{10}$ phages can easily be prepared. Thus, a complete pepscan of the entire genome of HIV can easily be accommodated within such a library.

In order to prepare the phage display library for a complete pepscan of the HIV genome, a substantially complete digest of the HIV genome would need to be prepared, as described above. Since HIV is a retrovirus, the complete HIV RNA would need to be reverse-transcribed into DNA. This DNA would then need to be substantially completely digested as this term is defined above and fragments of the desired size range separated. For example, the DNA could be incubated with DNAase I under appropriate conditions and fragments of from about 75 to about 150 bp could be separated. These fragments would then be cloned into a coat protein gene of an appropriately cut filamentous phage vector, for example the pIII gene of the fUSE5 vector, or a pVIII vector used in conjunction with a helper phage or other method to produce hybrid phages [Greenwood, J., Willis, A. E. and R. N. Perham, J. Mol. Biol., 1991, 220:821–827; and Willis, A. E., Perham, R. N. and D. Wraith, Gene, 1993, 128:79–83]. Now the complete pepscan of the HIV genome is in a phage display library.

Further examples of phage display libraries containing a complete pepscan of the genome of an organism can also be given. For example, the typical bacterial genome is about one million bp, or $10^6$ bp. About $3*10^5$ peptides of the desired size range would therefore be necessary, so that a library of about $6*10^6$ phage would be required for one-fold coverage, of which about five percent would be viable. Such a library could be prepared for *Mycobacterium tuberculosis*, a bacteria which was previously described in the Background section above, by using the above methods. Alternatively, libraries could be prepared for any bacterium and especially pathogenic bacterium.

Other examples of organisms include yeast, which has a genome of about $10^7$ bp. A library of about $6*10^7$ phage would be required for a complete pepscan of the yeast genome. As noted above, the preparation of such a library would involve the substantially complete digestion of the yeast genome, and separating DNA fragments of the desired size. These fragments would then be cloned into the desired phage gene, to form the phage display library.

Still other examples of organisms for which such phage display libraries can be constructed include parasites, which typically have genomes of about 100 million bp, or $10^8$ bp, as described above. Examples of such parasites are those which cause leishmaniasis, including *Leishmania major* and *L. braziliensis braziliensis*. Another example of a parasite is *Plasmodium falciparum*, which causes malaria. A phage display library of a complete pepscan of any one of these parasites could be prepared as described above.

Thus, a phage display library could clearly be prepared for a number of organisms, including, but not limited to, viruses including, but not limited to, retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis, salmonella, staphylococcus* species such as *Staph. aureus*, and *shigella*; parasites including, but not limited to, *plasmodium* species such as *Plasmodium falciparum, leishmania* species such as *Leishmania major* and *L. braziliensis braziliensis, entamoeba* species, *giardia* species, trichomonas species and *trypanosoma* species; and yeasts including, but not limited to, *Candida albicans*.

Example 2

Methods of Constructing a Bacterial Display Complete Pepscan Library

As noted above, a complete pepscan can be displayed in a phage library. However, phages are not the only display system for a complete pepscan. The basic principles behind such a library can be extended to a bacterial display or expression library.

The first step in preparing a bacterial display library, as in preparing a phage display library, is to substantially completely digest the genome of the organism of interest, or a portion of the genome of the organism of interest. Such a digest can be prepared according to the methods given in Example 1 above.

In the second step, the fragments from such a digest can be cloned into a vector, such as a phage, a plasmid, a phagmid or a cosmid. Examples of commercially available prokaryotic vectors include pKK223-3 and pTrc99, both available from Pharmacia Biotech. Such vectors are well known in the art. Although a phage can act as a vector, the phage itself does not display the peptide on its outer coat. Similarly, the other vectors are used only to introduce DNA fragments into the bacteria, but are not themselves used to display the foreign peptides.

Finally, the vector, with the inserted fragments from the digest, is transfected into the bacterial strain of choice. Again, transfection procedures are well known in the art. These bacteria then produce the peptide coded for by the fragment from the digest. These peptides can accumulate within the cell. Alternatively, they can be displayed on the cell wall of the bacteria, for those bacteria which display proteins or peptides on their cell wall. Alternatively and preferably, they can be secreted into the bacterial growth media, from which they can be collected.

A bacterial expression library containing a complete pepscan of the genome of an organism could be prepared for any of the organisms noted above, including, but not limited to, viruses including, but not limited to, retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis, salmonella, staphylococcus* species such as *Staph. aureus*, and *shigella*; parasites including, but not limited to, *plasmodium* species such as *Plasmodium falciparum, leishmania* species such as *Leishmania major* and *L. braziliensis braziliensis, entamoeba* species, *giardia* species, *trichomonas* species and *trypanosoma* species; and yeasts including, but not limited to, *Candida albicans*.

Example 3

Methods of Constructing an Eukaryotic Display Complete Pepscan Library

As noted in Example 2, bacteria can be used to construct an expression library for a complete pepscan. However, there are some disadvantages to using bacteria or phages, particularly for eukaryotic genomes. First, it is well known in the art that folding of eukaryotic proteins is not always done correctly by bacteria, which could be problematic for a peptide of sufficient length, such as a peptide of greater than about twenty residues. Second, correct post-translational modification of eukaryotic proteins is typically only performed by eukaryotes. Thus, a eukaryotic display complete pepscan library could be used to solve these problems.

Such a library would be constructed in the following way. First, a substantially complete digest of the genome of the organism of interest, or of a portion of the genome of interest, is prepared, as described in Examples 1 and 2 above. Second, the fragments from the digest are cloned into a eukaryotic expression vector. Both such vectors and such methods are well known in the art. For example, commercially available vectors include pSVK 3 and pBPV, both available from Pharmacia Biotech. Finally, the eukaryotic expression vector, with the inserted fragment from the digest, is transfected into an appropriate eukaryotic system. The eukaryotic cell then produces the peptide as part of a conjugate to an eukaryotic protein. This conjugate can accumulate internally, be expressed on the wall of the cell or secreted into the eukaryotic growth media. A particular advantage of such a conjugate is that unlike a bacterial protein, an eukaryotic protein may have limited or no immunogenicity, which may be important if repeated immunization is required.

Examples of such systems include yeast and mammalian cell lines, such as Cos-1, which is an immortal cell line. However, such transfections do not need to be performed only on isolated cells. For example, the eukaryotic expression vector, with the inserted fragment, could be introduced into cells of a whole eukaryote, without first removing those cells from the eukaryote. For example, the expression vector and inserted fragment could be introduced into macrophages of a horse, or of a human, such that those macrophages would then produce the peptide coded for by the inserted DNA fragment.

An eukaryotic expression library containing a complete pepscan of the genome of an organism could be prepared for any of the organisms noted above, including, but not limited to, viruses including, but not limited to, retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis, salmonella, staphylococcus* species such as *Staph. aureus*, and *shigella*; parasites including, but not limited to, *plasmodium* species such as *Plasmodium falciparum, leishmania* species such as *Leishmania major* and *L. braziliensis braziliensis, entamoeba* species, *giardia* species, *trichomonas* species and *trypanosoma* species; and yeasts including, but not limited to, *Candida albicans*.

Example 4

Methods of Preparing an Active Vaccine from a Complete Pepscan Library and Methods of Vaccinating an Organism with the Vaccine As noted above in Examples 1–3, there are a number of methods of preparing a complete pepscan library of a protein or proteins, or of a complete genome of an organism. Once such a library has been prepared, it has a number of potential uses, one of which is as a component of an active vaccine.

As described in the Background section above, an active vaccine causes at least one epitope of a first organism to be presented to the immune system of a second organism, which is the organism to be vaccinated. It should be noted, however, that in the case of autoimmune reactions, treatment of cancerous cells, or cells exhibiting inappropriate activity for the stage in the life cycle of the organism, the first and second organisms are effectively the same organism. Thus, the "epitope of the first organism" is actually an epitope expressed by a cancerous cell or a cell exhibiting inappropriate activity for the stage in the life cycle of the organism. Alternatively, in the case of autoimmune reactions such as myasthenia gravis, lupus or rheumatoid arthritis, the "epitope of the first organism" is normally expressed, but the immune reaction is inappropriate. In any case, the terms "first" and "second" organism are used below for clarity, it being understood that the "first" and "second" organisms can be the same organism.

Thus, since the complete pepscan libraries described in Examples 1–3 cause a peptide from a complete pepscan to be displayed, and since such a peptide constitutes an epitope or a collection of contiguous epitopes of the first organism, clearly these complete pepscan libraries can be used for presenting immunogenic epitopes. An active vaccine can therefore be prepared as follows.

First, a complete pepscan display library is prepared as described in Examples 1–3. The first organism, whose genome, or a portion of the genome, is used for the complete pepscan, can include, but is not limited to, viruses including, but not limited to, retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis, salmonella, staphylococcus* species such as *Staph. aureus*, and *shigella*; parasites including, but not limited to, *plasmodium* species such as *Plasmodium falciparum, leishmania* species such as *Leishmania major* and *L. braziliensis braziliensis, entamoeba* species, *giardia* species, *trichomonas* species and *trypanosoma* species; and yeasts including, but not limited to, *Candida albicans*.

Next, the complete pepscan display library is placed in a vaccine carrier. The vaccine carrier is a pharmaceutical composition, which may include thickeners, carriers, buffers, diluents, surface active agents, preservatives, and the like, all as well known in the art. Pharmaceutical compositions may also include one or more active ingredients such as but not limited to immune-system stimulating agents, known in the art as adjuvants, and the like in addition to the complete pepscan library. For example, the vaccine carrier can include pharmaceutically appropriate buffers. Alternatively, if a complete pepscan library is prepared according to Example 1, the vaccine carrier can include a plurality of phages which present the peptides of the complete pepscan, preferably filamentous phages. Most preferably, the DNA fragments are inserted into a coat protein of the phage, optionally pIII or pVIII. In this case an adjuvant may not be required as the phages themselves act as immune system stimulants [Greenwood, J., Willis, A. E. and R. N. Perham, J. Mol. Biol., 1991, 220:821–827; and Willis, A. E., Perham, R. N. and D. Wraith, Gene, 1993, 128:79–83].

Optionally, if a complete pepscan library is prepared according to Example 2, the DNA fragments are inserted into genetic material of the bacteria, so that the complete pepscan can be produced by a plurality of bacteria which synthesize the peptides of the pepscan. Since bacteria themselves are both highly immunogenic, as well as potentially hazardous to administer directly to the organism to be immunized, substantially only the synthesized peptides should be included in the vaccine carrier. Preferably the peptides are cloned as conjugates to a secreted bacterial protein, to facilitate purification. These conjugates are then collected from the bacterial growth media and purified from other media constituents. Proper selection of the bacterial protein can eliminate the need for an adjuvant, as the bacterial protein itself can act as the adjuvant.

Also optionally, if a complete pepscan library is prepared according to Example 3, the vaccine carrier can include the eukaryotic expression vector itself, so that the complete pepscan is presented by the vector. The method of Example 3 can be somewhat modified, in the following manner. Instead of transfecting eukaryotic cells with the eukaryotic expression vector containing the inserted DNA fragment, the eukaryotic expression vector itself can be placed in the vaccine carrier. The combination of the eukaryotic expression vector and the vaccine carrier is an example of a "naked DNA vaccine", as described in the Background above.

Once the vaccine has been prepared according to one of the above methods, it can be administered to an organism in a number of ways, which are well known in the art. For example, administration may be done topically (including ophtalmically, vaginally, rectally, intranasally), orally, by inhalation, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on responsiveness of the immune system of the organism to be vaccinated, but will normally be an initial dose of the vaccine. If necessary a booster dose or doses can be administered at a later date to achieve a desired level of protection against the first organism, as measured by antibody titer, for example. Persons of ordinary skill in the art can easily determine optimum dosages, dosing methodologies and repetition rates.

Examples of organisms to which such a vaccine could be administered include, but are not limited to, humans, pets such as dogs and cats, farm animals such as horses, pigs, sheep, cattle (both beef and dairy) and goats, laboratory animals such as mice, rats, monkeys and rabbits, and wild animals in captivity such as elephants, lions, tigers and bears, and other mammals, fish including, but not limited to, trout, salmon, carp and tuna, and birds, including, but not limited to, poultry such as chickens and turkeys, ducks and geese.

Example 5

Methods of Preparing a Discontinuous Library

The methods of Examples 1–4 all describe methods of preparing and using complete pepscan display libraries. However, the libraries prepared according to Examples 1–4 all contain continuous pepscans. That is, the DNA fragments code for a continuous peptide, which represents a faithful primary conformation of a fragment of the antigen or epitope. However, as noted in the Background section above, many epitopes are discontinuous. In order to display these epitopes in a library, a different library, referred to herein as a discontinuous library, is required.

A discontinuous library can be prepared as follows. First, a digest of the genetic material of a single biological unit or a portion thereof is prepared, by cutting at least a portion of the genome of an organism into fragments. This portion of the genome should represent at least a portion or part of a single biological unit of the organism. The single biological unit preferably has a discrete biological function.

The digest of the genetic material is preferably substantially complete, such that DNA fragments initiate at substantially every possible base pair. Alternatively, it can be a partial digest, such that DNA fragments initiate at a subset of substantially every possible base pair. In either case, an enzyme can be used to perform the digest. For a substantially complete digest of the DNA, the enzyme DNAase I is often used. As noted for Example 1, DNAase I cuts DNA relatively randomly; that is, it cuts between any two bases with relatively equal efficiency. When DNAase I is incubated with DNA under appropriate conditions, a collection of fragments is obtained which initiate at substantially every single possible base pair. This collection of fragments is a substantially complete digest of the genome of the organism.

For a partial digest, enzymes with greater specificity can be used, under appropriate conditions for activity of the enzyme. For example, the enzyme EcoRI recognizes the following sequence:

```
  123456
1 GAATTC
2 CTTAAG
```

EcoRI then cuts between G and A on strand 1 (bases 1 and 2), and between A and G on strand 2 (bases 5 and 6). Preferably, enzymes which cut more frequently, such as SauIIIA, are used. SauIIIA recognizes a four-base sequence and so is more likely to encounter the appropriate sequence on the DNA. Alternatively, a combination of such enzymes are used. DNAase I can also be used under appropriate conditions such that the DNA is only partially digested, for example by limiting the amount of time that DNAase I is allowed to cleave the DNA, or by reducing the concentration of DNAase I.

Optionally, either a substantially complete or a partial digest could be prepared by mechanical shearing of the DNA. Such mechanical shearing is well known in the art, and can be accomplished by sonication of the DNA, for example.

After the digest, either partial or substantially complete, has been prepared, the resulting fragments are processed so that these fragments have appropriately cut ends, by enzymatic degradation or synthesis for example. Those fragments which fall within a desired size range are then separated from the collection of fragments. At least two of the resulting DNA fragments are ligated together under appropriate conditions according to methods which are well known in the art. This ligation results in at least one ligation product, which is simply a single DNA segment formed by ligating at least two of the DNA fragments from the digest. Preferably, appropriate conditions are used for ligation so that more than two of the fragments ligate per ligation product.

The ligation product is then digested again to form DNA fragments, which are then preferably sorted by size to separate those fragments which fall within the desired size range. Preferably this size range is larger than the size range from the first digest. Similarly to the first digest, this second digest can either be partial or substantially complete, and can be performed according to a variety of methods, including but not limited to, enzymatic and mechanical. If a substantially complete digest is desired, DNAase I can be used, by incubating the ligation product with DNAase I under appropriate conditions, in order to obtain at least one DNA fragment. If a partial digest is desired, again restriction enzymes such as EcoRI, SauIIIA or even DNAase I can be used under the appropriate conditions, as described above. Alternatively, mechanical shearing can be used, by sonication of the ligation product for example. In any case, if desired, DNA fragments which fall within a desired size range can be separated from the rest of the digest.

Each of such DNA fragments is a conformational fragment; that is, a fragment which is potentially capable of representing a discontinuous epitope. As noted above, a discontinuous epitope includes the novel contiguous presentation of two different amino acid sequences which were previously discontinuous in the original primary amino acid sequence. The discontinuous library includes the DNA fragment or fragments obtained from this second digestion, whether partial or substantially complete. Optionally, the discontinuous library can include a display carrier for the DNA fragment or fragments. Preferably, the display carrier includes one of several optional components and is prepared according to one of several preferred methods as described hereinbelow. Preferred Method 1: One optional component is a plurality of bacteria, so that the DNA fragment or fragments are inserted into genetic material of the bacteria, according to Example 2. Preferred Method 2: Another optional component is a plurality of phages, so that the DNA fragment or fragments are inserted into genetic material of the phages, according to Example 1.

Preferred Method 3: Yet another optional component is a eukaryotic expression vector, so that the DNA fragments are inserted into the expression vector, according to Example 3. Optionally, the eukaryotic expression vector can be transfected into eukaryotic cells, according to Example 3.

The number of components within the display carrier which are required for a substantially complete representation of a single biological unit in a discontinuous library depend upon a number of factors, such as the type of display carrier, the number of DNA basepairs required to represent the single biological unit, the size of fragments desired from both digests, the extent of both digests and the extent of ligation. However, since the single biological unit typically requires fewer DNA basepairs for representation than a substantially complete genome, clearly a single biological unit could be accommodated by a single library.

The advantage of the discontinuous library is that it can represent discontinuous epitopes, as noted above. However, in order to reduce the production of illogical or artifactual, biologically irrelevant "epitopes", the genetic material used to produce the library must represent at least a portion of a single biological unit with a biological function. Examples of such biological units include, but are not limited to, a protein, a group of proteins such as a cytoskeleton, and non-protein structures such as a tRNA, ribozymes or a telomere.

The preparation of a discontinuous library for a protein or a portion of a protein would thus give information about dipeptide juxtapositions within that protein or portion of protein. These dipeptide juxtapositions arise during folding of the protein into its three dimensional structure, when a peptide from one location on the primary amino acid chain is folded next to another peptide from a completely different location on the primary amino acid chain. An epitope taken from the primary amino acid chain which faithfully represents the primary conformation of the protein could never represent such a dipeptide juxtaposition.

Similarly, a discontinuous library could also give information about dipeptide juxtapositions within a group of proteins or quaternary structure, such as a cytoskeleton. The cytoskeleton is composed of a number of different proteins, including tubulin and actin. Since tubulin and actin are completely different proteins, a single epitope from the primary amino acid chain of either protein could never represent a dipeptide juxtaposition of both proteins. However, a discontinuous library prepared from the genes encoding both proteins could represent such dipeptide juxtapositions. Indeed, a discontinuous library could even give information about transient interactions of two or more proteins, such as the binding of gp120 to CD4, for example.

Also, a discontinuous library could be used to represent non-protein structures such as a tRNA, ribozymes or a telomere. A tRNA and a ribozyme are RNA molecules folded into three dimensional structures, while a telomere is the DNA at the ends of a chromosome, which also assumes a particular structure. Since the discontinuous library includes genetic material, such as DNA or RNA, prepared according to the above method, clearly the structure of the telomere itself could be examined using the discontinuous library. The RNA could also be prepared by taking the DNA which codes for the tRNA, preparing a discontinuous library as described above, and then making RNA from the DNA, using in vitro transcription methods well known in the art.

Example 6

Methods of Preparing an Active Vaccine from a Discontinuous Library and Methods of Vaccinating an Organism with the Vaccine As noted above in Example 5, there are a number of methods of preparing a discontinuous library. Once such a library has been prepared, it has a number of potential uses, one of which is as a component of an active vaccine.

As described in the Background section above, an active vaccine causes at least one epitope of a first organism to be presented to the immune system of a second organism, which is the organism to be vaccinated.

Thus, since the discontinuous libraries described in preferred embodiments of Example 5 can cause a discontinuous or discontinuous epitope of an organism to be displayed, clearly these discontinuous libraries can be used to cause immunogenic epitopes to be displayed. An active vaccine can therefore be prepared as follows.

First, a discontinuous library is prepared as described in Example 5, preferably with a display carrier. The first organism, whose genome is used for the discontinuous library, can include, but is not limited to, viruses including but not limited to retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis, salmonella, staphylococcus* species such as *Staph. aureus*, and *shigella*; parasites including, but not limited to, *plasmodium* species such as *Plasmodium falciparum, leishmania* species such as *Leishmania major* and *L. braziliensis braziliensis, entamoeba* species,

*giardia* species, *trichomonas* species and *trypanosoma* species; and yeasts including, but not limited to, *Candida albicans*.

Next, the discontinuous library is placed in a vaccine carrier. The vaccine carrier is a pharmaceutical composition, which may include thickeners, carriers, buffers, diluents, surface active agents, preservatives, and the like, all as well known in the art. Pharmaceutical compositions may also include one or more active ingredients including, but not limited to, immune-system stimulating agents and the like in addition to the discontinuous library. For example, the vaccine carrier can include pharmaceutically appropriate buffers. Alternatively, if a discontinuous library is prepared according to Preferred Method 1 of Example 5, the vaccine carrier can include a plurality of phages, preferably filamentous phages. Most preferably, the DNA fragments are inserted into a gene for a coat protein of the phage, optionally pIII or pVIII.

Optionally, if a discontinuous library is prepared according to Preferred Method 2 of Example 5, the DNA fragments are inserted into genetic material of the bacteria, so that the complete pepscan can be produced by a plurality of bacteria which synthesize the peptides of the pepscan as part of a conjugate to a bacterial protein. Since bacteria themselves are both highly immunogenic, as well as potentially hazardous to administer directly to the organism to be immunized, substantially only the conjugates should be included in the vaccine carrier. These conjugates can be allowed to accumulate in the bacterial cell, but preferably include a secreted bacterial protein so that the conjugate is secreted by the bacteria, to facilitate collection of the conjugate from the growth media.

Also optionally, if a discontinuous library is prepared according to Preferred Method 3 of Example 5, the vaccine carrier can include the eukaryotic expression vector itself. Preferred Method 3 of Example 5 can be somewhat modified, in the following manner. Instead of transfecting eukaryotic cells with the eukaryotic expression vector containing the inserted DNA fragment, the eukaryotic expression vector itself can be placed in the vaccine carrier. The combination of the eukaryotic expression vector and the vaccine carrier is an example of a "naked DNA vaccine", as described in the Background above.

Once the vaccine has been prepared according to one of the above methods, it can be administered to the organism to be vaccinated in a number of ways, which are well known in the art. For example, administration may be done topically (including ophtalmically, vaginally, rectally, intranasally), orally, by inhalation, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on responsiveness of the immune system of the organism to be vaccinated, but will normally be include an initial dose of the vaccine. If necessary a booster dose or doses can administered at a later date to achieve a desired level of protection against the first organism, as measured by antibody titer, for example. Persons of ordinary skill in the art can easily determine optimum dosages, dosing methodologies and repetition rates.

Examples of organisms to which such a vaccine could be administered include, but are not limited to, humans, pets such as dogs and cats, farm animals such as horses, pigs, sheep, cattle (both beef and dairy) and goats, laboratory animals such as mice, rats, monkeys and rabbits, and wild animals in captivity such as elephants, lions, tigers and bears, and other mammals, fish such as trout, salmon, carp and tuna, and birds such as poultry, including chickens and turkeys, ducks and geese.

Example 7

Methods of Preparing a Conformational Peptide

A conformational peptide is a peptide which represents a discontinuous epitope, as described in the Background section above. Such a peptide can be prepared by first preparing a discontinuous library, according to the method of Example 5. Second, the discontinuous library is inserted into an expression system, which synthesizes the peptide. Examples of such an expression system include, but are not limited to, viral, bacterial, eukaryotic, and artificial.

A phage display system can be prepared as follows. First, the discontinuous library can be cloned into the phage. Since the discontinuous library of this embodiment is actually at least one DNA fragment, at least one phage is prepared to receive the at least one fragment. This is accomplished by modifying a gene of the phage, so that the fragment can be cloned into the phage gene. The product of that gene, a phage protein, will then include a foreign peptide. The sequence of the foreign peptide will depend upon the inserted DNA fragment. Preferably, a gene for a coat protein is used, so that the phage will display the foreign peptide on its outer surface. Typically, filamentous phages are used because they have coat proteins which are easily modified to receive the DNA fragment. The preferred coat proteins are pIII and pVIII. pIII can tolerate insertions of foreign peptides of up to a few hundred amino acids in length, but only five copies of pIII are on the phage coat. About 2700 copies of pVIII are on the phage coat, but pVIII can only tolerate insertions of five or six amino acids, unless special rescue methods are used. The choice of a particular coat protein depends upon both the length of the foreign peptide and upon the desired number of copies of the foreign peptide.

Once the particular coat protein has been chosen, the gene is modified to contain a unique blunt end restriction site, preferably at its N terminal region, using methods which are well known in the art. The particular nature of the restriction site depends upon the strain of phage which is used. For example, for the pIII construct of the fUSE5 vector of the filamentous phage fd-tet such a site could be inserted between the two Sfi-1 sites present on the vector. However, it is possible to construct many such blunt-ended phage vectors, by manipulating restriction sites so that DNA fragments can be inserted where desired. Alternatively, oligonucleotide linkers can be used to clone the DNA fragments in distinct and unique restriction sites in the vector which are not necessarily blunt-ended.

Finally, the fragment or fragments from the digest of the ligation product is cloned into the appropriately cut phage vector, using methods which are well known in the art.

A second system is a bacterial expression system. First, the discontinuous library can be cloned into the vector, such as a phage, a plasmid, a phagmid or a cosmid. Such vectors are well known in the art. Although a phage can act as a vector, the phage itself does not display the peptide on its outer coat. Similarly, the other vectors are used only to introduce DNA fragments into the bacteria, but are not themselves used to display the foreign peptides. Since the discontinuous library of this embodiment is actually at least one DNA fragment, at least one vector is prepared to receive the at least one fragment.

Finally, the vector, with the inserted fragment from the digest, is transfected into the bacterial strain of choice. Again, transfection procedures are well known in the art. These bacteria then produce the peptide coded for by the fragment from the digest. These peptides can accumulate within the cell. Alternatively, they can be displayed on the cell wall of the bacteria or secreted into the bacterial growth media, from which they can be collected.

A third expression system is a eukaryotic expression system, which is prepared as follows. The fragment or fragments from the second digest are cloned into a eukaryotic expression vector. Both such vectors and such methods are well known in the art. For example, commercially available vectors include pSVK 3 and pBPV, both available from Pharmacia Biotech. Next, the eukaryotic expression vector, with the inserted fragment from the digest, is transfected into an appropriate eukaryotic system. Again, transfection procedures are well known in the art. These eukaryotic cells then produce the peptide coded for by the fragment from the digest. These peptides can accumulate within the cell. Alternatively, they can be displayed on the cell wall of the eukaryote or secreted into the eukaryotic growth media, from which they can be collected.

Examples of such eukaryotic systems include yeast and mammalian cell lines, such as Cos-1, which is an immortal cell line. However, such transfections do not need to be performed only on isolated cells. For example, the eukaryotic expression vector, with the inserted fragment, could be introduced into cells of a whole eukaryote, without first removing those cells from the eukaryote. For example, the expression vector and inserted fragment could be introduced into the macrophages of a horse, or of a human, such that those macrophages would then produce the peptide coded for by the inserted DNA fragment.

Furthermore, the continuous peptide itself has a number of uses. For example, the continuous peptide could be used to block a ligand binding to a receptor, such as gp120 binding to CD4. Alternatively, the peptide could act a molecular decoy, by binding a protein or peptide.

Example 8

Methods of Synthesizing and of Detecting an Antibody for Binding a Discontinuous Epitope As noted above in the Background section, discontinuous and continuous epitopes of a first organism can be bound by antibodies which are produced by the immune system of a second organism, also referred to as the organism to be vaccinated. Methods of detecting antibodies which bind continuous epitopes are well known in the art, and generally involve screening immune material which contains at least one antibody.

The immune material which is screened can be prepared by administering a vaccination entity to the second organism. Optionally, the vaccination entity can include at least a portion of the single biological unit of the first organism. Alternatively, the vaccination entity can include a discontinuous library. The discontinuous library can be prepared according to Example 5, using Preferred Method 1, 2 or 3. Each of these methods results in the preparation of a discontinuous library which is presented by a display carrier, which can also be an expression carrier. The display carrier can be a phage display library, bacterial expression library or an eukaryotic expression library, depending upon the method which is used.

Optionally, the immune material which is screened can include serum with at least one antibody. For example, such serum could be obtained from a human patient who has been infected by, or immunized against, the first organism. Alternatively, such serum could be obtained from an animal, including, but not limited to, a rabbit or a mouse, which has been infected by, or immunized against, the first organism.

Also optionally, the immune material can include polyclonal antibodies. Polyclonal antibodies can be prepared by injecting a rabbit or an animal with a larger blood volume such as a horse, for example, with a substance or substances which provoke an immune response. Such substances can include, but are not limited to, substantially the entire first organism, or whole or partial proteins from the first organism. The rabbit or horse then produces polyclonal antibodies in response to these substances. Such antibodies are called "polyclonal" because they are derived from more than one B-cell clone.

Monoclonal antibodies, on the other hand, bind to only one epitope of the pathogen. Monoclonal antibodies are obtained from hybridomas, which are produced by fusing spleen-derived B cells which secrete a single antibody, with non-antibody-secreting myeloma cells. Such cells can be prepared from mice cells, for example, or by immortalization of human B-cells by EBV (Epstein-Barr virus), for example.

Once the immune material has been prepared, similar methods to those well known in the art can be used to detect antibodies which bind discontinuous epitopes of a single biological unit of the first organism. As a first step, a screening entity is prepared. This screening entity can include a discontinuous library which is prepared according to Example 5, using Preferred Method 1, 2 or 3. Each of these methods results in the preparation of a discontinuous library which is presented by a display carrier. The display carrier can be a phage display library, a bacterial expression library or an eukaryotic expression library, depending upon the method which is used. Alternatively, the screening entity can include at least a portion of the single biological unit which contains the discontinuous epitope of interest. However, the screening entity should not be identical to the vaccination entity.

After the screening entity has been chosen, it is screened with immune material which contains at least one antibody. Such screening can be performed in a number of different ways which are well known in the art, and some of which are described in *Molecular Biology of the Cell*.

For example, the screening entity can be substantially immobilized on a solid support. Examples of such solid supports include, but are not limited to, porous membranes such as nylon and nitrocellulose, non-porous films such as polypropylene, or plastics. The immune material can then be incubated with the screening entity under appropriate conditions, so that any antibody or antibodies can bind to the appropriate epitope or epitopes, as presented by the screening library [Smith, G. P. and J. K. Scott, Methods in Enzymol., 1993, 217:228–257].

Finally, the presence of the bound antibody or antibodies can be detected in a variety of ways, which are well known in the art. For example, the antibody or antibodies can be directly labelled with a substance which acts as a marker for the presence of the antibody or antibodies. Examples of such substances include, but are not limited to, fluorescent dyes or radioactive substances. Alternatively, greater sensitivity can be obtained by using a secondary antibody-which can bind to a variety of antibodies. The secondary antibody can be labelled as above. Optionally, an ELISA (enzyme-linked immunoassay) can be used, in which an enzyme, such as alkaline phosphatase, is linked to the secondary antibody. A substrate is incubated with the enzyme, and a sensitive chemical test is used to detect the presence of the enzymatic product.

Once the antibody has been detected, the antibody can then be obtained from the immune material, by a number of methods which are well known in the art, for example, protein purification methods including, but not limited to, chromatography.

Example 9

Methods of Preparing a Passive Vaccine and Methods of Vaccinating an Organism with the Vaccine A passive vaccine is one which already contains an antibody or antibodies against a particular epitope or epitopes, as opposed to an active vaccine, which attempts to stimulate the immune system to produce such antibodies. Passive vaccines can be prepared against discontinuous epitopes according to the following procedure. First, at least one antibody which binds at least one discontinuous epitope is detected, as described above in Example 8. Such an antibody can also be synthesized according to the methods given in Example 8.

Next, the antibody is placed in a vaccine carrier, according to Example 4. Examples of organisms to which such a vaccine could be administered include, but are not limited to, those given in Example 4.

Example 10

A Diagnostic Tool for Detecting an Organism by Using a Conformational Unit

Frequently it is desirable to diagnose the presence of an immune response to a particular organism in a tissue or blood sample, or even in vivo. Such detection can be accomplished by using a conformational peptide which represents an epitope of the organism of interest, putting the immune material which includes at least one antibody, such as the blood or tissue sample, in contact with the conformational peptide, and then by using a detection assay to detect antibody binding to the conformational peptide. A diagnostic tool which can perform such a diagnosis has many potential biomedical uses, including the detection of organisms including, but not limited to viruses including but not limited to retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis, salmonella, staphylococcus* species such as *Staph. aureus*, and *shigella*; parasites including, but not limited to, *plasmodium* species such as *Plasmodium falciparum, leishmania* species such as *Leishrnania major* and *L. braziliensis braziliensis, entamoeba* species, *giardia* species, *trichomonas* species and *trypanosoma* species; and yeasts including, but not limited to, *Candida albicans*. Certainly, such diagnostic tools are known for detecting the presence of HIV for example. However, these tools generally do not rely upon antibodies which have been specifically prepared to bind discontinuous epitopes.

A novel diagnostic tool can be constructed from a conformational peptide representing at least one discontinuous epitope of a single biological unit of the organism of interest, and a detection assay for determining when an antibody is actually bound to the discontinuous epitope. It should be noted that although this description uses a "conformational peptide", it could be extended to include a discontinuous library as described above in Example 5. Both a conformational peptide and a discontinuous library are hereinafter collectively known as a "conformational unit". The conformational peptide is prepared according to one of the methods of Example 7. These detection assays can employ a detection moiety attached to the conformational peptide, a density gradient, or a chromatograph. Such a detection moiety can include fluorescent dyes such as rhodamine or fluorescein. These dyes can be detected by a spectrophotometer, for example.

Density gradients are well known in the art, and are prepared in the following manner. First, a density gradient is prepared by layering materials of different densities within a container, such as a tube. The material with the highest density is substantially near the bottom of the container, while the material with the lowest density is substantially near the top of the container. An example of such a material is a sucrose solution with varying concentrations of sucrose. The higher the concentration of sucrose, the higher the density of the solution.

After the density gradient has been prepared, a solution containing the conformational peptide and antibody or antibodies of interest is placed on top of the material with the lowest density, being careful not to disturb the gradient. The container with the density gradient is then subjected to ultracentrifugation. A conformational peptide which has been bound by an antibody will have a different density, and hence will move to a different layer, as compared to a conformational peptide which has not been bound by such an antibody. Therefore, each will migrate to a different position along the gradient. After ultracentrifugation, the location of the conformational peptide within the gradient can be detected according to methods which are well known in the art.

Yet another example of a detection assay employs a chromatograph. A chromatograph is a device for separating proteins according to some property. For example, proteins can be separated according to their relative solubility by thin-layer chromatography. In this procedure, a sample which includes proteins in solution is applied to a thin layer of absorbent material, such as cellulose or silica gel, which has been attached to a sheet of stiff material such as plastic or glass. At least one solvent is introduced to one edge of the absorbent material. As the solvent front moves through the absorbent material, the proteins are separated according to their relative solubility in the solvent. Alternatively, proteins can be separated by column chromatography, in which a sample which includes proteins in solution is applied to one end of a column containing a porous solid. Such a porous solid then separates the proteins by size, or by some other property. Clearly, any of these chromatographs could be used to separate a conformational peptide which is bound by an antibody of interest from a conformational peptide which is not so bound.

Thus, this diagnostic tool could be used as follows. First, the conformational unit, either conformational peptide or discontinuous library, is incubated with a sample containing an antibody. A sample is simply defined as containing an antibody, including, but not limited to, a portion of tissue or blood and immune material. "Incubated" is simply defined as allowing the sample to come in contact with the conformational unit under conditions which are appropriate for permitting the binding of the antibody to the conformational unit. For example, an appropriate buffer or buffers could be included, and the sample and conformational unit could be maintained at an appropriate temperature. Next, the detection assay, as described above, could be performed to determine when the conformational unit is bound by the antibody.

Example 11

A Diagnostic Tool for Detecting an Organism with an Antibody

Frequently it is desirable to diagnose the presence of a particular organism in a tissue or blood sample, or even in vivo. Such detection can be accomplished by using an antibody or antibodies which bind to at least one epitope of the organism of interest, and then by using a detection assay to detect antibody binding. A diagnostic tool which can perform such a diagnosis has many potential biomedical uses, including the detection of organisms including, but not limited to, viruses including but not limited to retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis, salmonella, staphylococcus* species such as *Staph. aureus*, and *shigella*; parasites including, but not limited to, *plasmodium* species such as *Plasmodium falciparum, leishmania* species such as *Leishmania major* and *L. braziliensis braziliensis, entamoeba* species, *giardia* species, *trichomonas* species and *trypanosoma* species; and yeasts including, but not limited to, *Candida albicans*. Certainly, such diagnostic tools are known for detecting the presence of HIV for example. However, these tools generally do not rely upon antibodies which have been specifically prepared to bind discontinuous epitopes.

A novel diagnostic tool can be constructed from an antibody for binding at least one discontinuous epitope of a single biological unit of the organism of interest, and a detection assay for determining when the antibody is actually bound to the discontinuous epitope. The antibody is prepared according to Example 8. These detection assays can employ a detection moiety attached to the antibody, a density gradient, or a chromatograph. Such a detection moiety can include fluorescent dyes such as rhodamine or fluorescein. These dyes can be detected by a spectrophotometer, for example.

Density gradients are well known in the art, and are prepared in the following manner. First, a density gradient is prepared by layering materials of different densities within a container, such as a tube. The material with the highest density is substantially near the bottom of the container, while the material with the lowest density is substantially near the top of the container. An example of such a material is a sucrose solution with varying concentrations of sucrose. The higher the concentration of sucrose, the higher the density of the solution.

After the density gradient has been prepared, a solution containing the antibody or antibodies of interest is placed on top of the material with the lowest density, being careful not to disturb the gradient. The container with the density gradient is then subjected to ultracentrifugation. An antibody which has bound a discontinuous epitope will have a different density, and hence will move to a different layer, as compared to an antibody which has not bound such an epitope. Therefore, each will migrate to a different position along the gradient. After ultracentrifugation, the location of the antibody within the gradient can be detected according to methods which are well known in the art.

Yet another example of a detection assay employs a chromatograph. A chromatograph is a device for separating proteins according to some property. For example, proteins can be separated according to their relative solubility by thin-layer chromatography. In this procedure, a sample which includes proteins in solution is applied to a thin layer of absorbent material, such as cellulose or silica gel, which has been attached to a sheet of stiff material such as plastic or glass. At least one solvent is introduced to one edge of the absorbent material. As the solvent front moves through the absorbent material, the proteins are separated according to their relative solubility in the solvent. Alternatively, proteins can be separated by column chromatography, in which a sample which includes proteins in solution is applied to one end of a column containing a porous solid. Such a porous solid then separates the proteins by size, or by some other property. Clearly, any of these chromatographs could be used to separate an antibody which is bound to a discontinuous epitope of interest from an antibody which is not so bound.

This diagnostic tool could be used as follows. First, the antibody could be incubated with a sample containing at least one discontinuous epitope of the first organism. A sample is simply defined as containing at least one discontinuous epitope of the organism, including, but not limited to, a portion of tissue or blood and immune material. "Incubated" is simply defined as allowing the sample to come in contact with the at least one discontinuous epitope under conditions which are appropriate for permitting the binding of the antibody to the at least one discontinuous epitope. For example, an appropriate buffer or buffers could be included, and the sample and antibody could be maintained at an appropriate temperature. Next, the detection assay is used for determining when the antibody is bound to the at least one discontinuous epitope of the organism.

Example 12

Method of Determining a Structure of a Protein with an Identified Gene and of Preparing a Filter for Such a Structure Determination As noted in the Background above, the three-dimensional, or tertiary, structure of a protein can provide useful information which can be exploited for developing new pharmaceuticals such as vaccines or drugs, and for many other purposes. However, determining such a protein structure can be difficult. Methods are known in the art which attempt to determine a protein structure from the primary amino acid sequence, but these methods are not usually very successful, simply because the "rules" for protein folding are not completely understood. More successful methods place constraints on such protein structure determinations, by obtaining information about the protein itself.

Such information can be obtained by NMR, which provides information about the interactions of atoms within the protein, as noted in the Background section above. However, NMR suffers from lack of specificity; that is, the interactions of too many atoms are all presented simultaneously, making it difficult to decipher the behavior of individual atoms. Furthermore, NMR requires large amounts of highly pure protein. A more specific method, using the interaction of fluorescent dye molecules attached to particular residues, was also described in the Background section above. However, this method requires that the protein be purified and labelled with dye molecules, which are non-trivial procedures.

A better method for determining specific interactions between parts of the protein, and hence for obtaining constraints in the form of a partial structure which can be used to determine the full protein structure, requires only that the protein has an identified gene. By "identified", it is meant that the gene is available and that the sequence of the gene is known. This method is as follows.

First, a conformational peptide of the protein of interest is prepared according to Example 7. Second, the conformational peptide is screened with a molecule. This molecule is characterized by having a known interaction with the protein of interest. By screening the conformational peptide with the molecule, a conformational peptide which represents a true dipeptide juxtaposition of the protein can be obtained. Methods of screening can include any method which permits detection of the binding of the molecule of interest to the protein itself, simply by substituting the conformational peptide for the protein in the assay.

Next, the amino acid sequence of the conformational peptide is determined. One method of determining the amino acid sequence is to determine the DNA sequence of the conformational fragment which codes for the conformational peptide. Alternatively, the conformational peptide can be directly sequenced, by hand or by machine, according to methods which are well known in the art. This sequence can be used to determine a dipeptide juxtaposition; that is, the two peptides of the protein which form a discontinuous epitope due to their relative locations in the folded protein. Such a dipeptide juxtaposition actually represents a partial structure of the protein, since it gives information about the relative location of two parts of the protein within the three-dimensional structure.

This partial structure can be used as a basis for deducing the substantially complete three-dimensional structure of the protein. For example, the partial structure can be used as a constraint, in order to limit the number of theoretical structures which must be examined. Such a constraint is similar to that derived from the interaction of fluorescent dye molecules attached to particular residues, as described in the Background above. Thus, clearly the general use of such constraints is well known in the art. However, the specific use of a dipeptide juxtaposition is clearly novel and non-obvious.

Furthermore, such a dipeptide juxtaposition can clearly be used as part of a filter for determining if a theoretical structure of a protein is non-biological. Such a filter would include a dipeptide juxtaposition of a protein as described above, and an algorithm for comparing the dipeptide juxtaposition to the theoretical structure, in order to determine if the theoretical structure is non-biological. Such algorithms are well known in the art, as described above in the Background, and include commercially available algorithms such as Delphi and Charmm. Further references include Havel, T. F. and K. J. Wutrich, J. Mol. Biol., 1985, 182: 281–294.

While the invention has been described with respect to a limited number of embodiments, it will be appreciated that many variations, modifications and other applications of the invention may be made.

What is claimed is:

1. A method of identifying and producing a peptide that interacts with a ligand that interacts with a discontinuous epitope of a single biological unit consisting of a single protein, or consisting of two or more proteins that interact to form a complex, the method comprising:
   (a) providing a plurality of DNA fragments consisting of fragments, each of which appears in a DNA sequence that encodes the single biological unit;
   (b) creating a library consisting of oligonucleotides from said plurality of DNA fragments, each said oligonucleotide comprising at least two contiguous fragments, said fragments being randomly ligated such that any oligonucleotide in the library can ligate with any other oligonucleotide in the library;
   (c) inserting each of said oligonucleotides from said library of oligonucleotides into an expression system;
   (d) causing the peptides encoded by said oligonucleotides to be expressed;
   (e) screening the expressed peptides for interaction with a ligand that interacts with a discontinuous epitope of said single biological unit;
   (f) identifying any peptide which so interacts; and
   (g) producing any peptide so identified.

2. A method in accordance with claim 1, wherein said procedure of (a) comprises cutting said DNA sequence to form said plurality of DNA fragments.

3. A method in accordance with claim 1, wherein said procedure of (b) comprises randomly ligating said plurality of DNA fragments to one another to form at least one ligated fragment and at least partially digesting said at least one ligated fragment to form said library of oligonucleotides.

4. A method of preparing a library of peptides that can be screened to find peptides that interact with ligands that interact with discontinuous epitopes of a single biological unit consisting of a single protein, or consisting of two or more proteins that interact to form a complex, comprising:
   (a) providing a plurality of DNA fragments consisting of fragments, each of which appears in a DNA sequence that encodes the single biological unit;
   (b) creating a library consisting of oligonucleotides from said plurality of DNA fragments, each said oligonucleotide comprising at least two contiguous fragments, said fragments being randomly ligated such that any oligonucleotide in the library can ligate with any other oligonucleotide in the library;
   (c) inserting each of said oligonucleotides from said library of oligonucleotides into an expression system; and
   (d) causing the peptides encoded by said oligonucleotides to be expressed, thereby preparing a library of peptides.

5. A method in accordance with claim 4, wherein said procedure of (a) comprises cutting said DNA sequence to form said plurality of DNA fragments.

6. A method in accordance with claim 4, wherein said procedure of (b) comprises randomly ligating said plurality of DNA fragments to one another to form at least one ligated fragment and at least partially digesting said at least one ligated fragment to form said library of oligonucleotides.

7. A method in accordance with claim 1, wherein each of said DNA fragments of (a) has a size of about 50 to about 150 base pairs.

8. A method in accordance with claim 4, wherein each of said DNA fragments of (a) has a size of about 50 to about 150 base pairs.

9. A method in accordance with claim 1, wherein said single biological unit consists of a single protein having a single definable sequence, or consists of two or more proteins, each having a single definable sequence, which proteins interact to form a complex.

10. A method in accordance with claim 4, wherein said single biological unit consists of a single protein having a single definable sequence, or consists of two or more proteins, each having a single definable sequence, which proteins interact to form a complex.

11. A method of identifying and producing a peptide which interacts with a ligand which interacts with a discontinuous epitope of a single biological unit consisting of a single protein or consisting of two or more proteins which interact to form a complex, the method comprising:

(a) providing a plurality of DNA fragments consisting of fragments, each of which appears in a DNA sequence that encodes the single biological unit;

(b) creating a library consisting of oligonucleotides from said plurality of DNA fragments, each said oligonucleotide comprising at least two contiguous fragments, said fragments being randomly ligated;

inserting each of said oligonucleotides from said library of oligonucleotides into an expression system;

causing the peptides encoded by said oligonucleotides to be expressed;

screening the expressed peptides for interaction with a ligand that interacts with a discontinuous epitope of said single biological unit;

identifying any peptide which so interacts; and producing any peptide so identified.

* * * * *